United States Patent [19]

VonKrusenstierna et al.

[11] 4,105,507
[45] Aug. 8, 1978

[54] METHOD AND SYSTEM FOR INSTANTANEOUSLY DETERMINING THE OXYGEN ACTIVITY IN MOLTEN METALS

[75] Inventors: Otto VonKrusenstierna; Anders Persson; Marja Widell, all of Vasteras, Sweden

[73] Assignee: Asea Aktiebolag, Vasteras, Sweden

[21] Appl. No.: 171,128

[22] Filed: Aug. 12, 1971

[30] Foreign Application Priority Data

Aug. 27, 1970 [SE] Sweden .............. 11627/70

[51] Int. Cl.$^2$ .............................. G01N 27/46
[52] U.S. Cl. .................. 204/1 T; 204/195 S; 73/23
[58] Field of Search .................. 204/1 T, 195.5 R

[56] References Cited

U.S. PATENT DOCUMENTS

| | | | |
|---|---|---|---|
| 2,183,531 | 12/1939 | Allison | 204/195 R |
| 3,400,054 | 9/1968 | Ruka et al. | 204/195 S |
| 3,454,486 | 7/1969 | Davies | 204/195 S |
| 3,514,377 | 5/1970 | Spacil et al. | 204/195 S |
| 3,616,407 | 10/1971 | Engell et al. | 204/195 S |
| 3,630,874 | 12/1971 | Olette et al. | 204/195 S |
| 3,645,720 | 2/1972 | Imai et al. | 204/195 S |
| 3,652,427 | 3/1972 | Flood et al. | 204/1 T |
| 3,713,995 | 1/1973 | Cherkason et al. | 204/1 T |

FOREIGN PATENT DOCUMENTS 1,191,222  5/1970  United Kingdom ............... 204/195 S Primary Examiner—T. Tung
Attorney, Agent, or Firm—Watson, Cole, Grindle & Watson

[57] ABSTRACT

A system for determining the oxygen activity in molten metals includes a measuring probe insertable in the melt and provided with an electrochemical cell, a thermoelement, and three contact devices. The probe is mounted at the end of a measuring lance. A preamplifier mounted on the lance is connected to the contact devices and furnishes the signals received to a preamplifier which supplies signals to a calculating unit which converts the EMF of the electrochemical cell and the EMF of the thermoelement to magnitudes representing the oxygen acitivity and the temperature, which are either recorded or observed on indicators.

The measuring probe is mounted in a paper sleeve which is removable attached to the end of the lance. The electrochemical cell includes a body of solid electrolyte passing through the outer end wall of the cell and connected to one of the contact devices.

4 Claims, 5 Drawing Figures

METHOD AND SYSTEM FOR INSTANTANEOUSLY DETERMINING THE OXYGEN ACTIVITY IN MOLTEN METALS

BACKGROUND OF THE INVENTION

Field of the Invention

The present invention relates to a system for determining the oxygen activity in molten metals. Particularly in the production of steel, it is extremely valuable to be able to determine the oxygen activity of the melt quickly. However, the invention can also be used for measurements in melts of other metals and metal alloys.

SUMMARY OF THE INVENTION

According to the invention, a system for determining the oxygen activity in molten metals includes a measuring probe insertable in the melt and provided with an electrochemical cell, a thermoelement, and three contact devices. The probe is mounted at the end of a measuring lance. A preamplifier mounted on the lance is connected to the contact devices and furnishes the signals received to a preamplifier which supplies signals to a calculating unit which converts the EMF of the electrochemical cell and the EMF of the thermoelement to magnitudes representing the oxygen activity and the temperature, which are either recorded or observed on indicators.

The measuring probe is mounted in a paper sleeve which is removably attached to the end of the lance. The electrochemical cell includes a body of solid electrolyte passing through the outer end wall of the cell and connected to one of the contact devices.

BRIEF DESCRIPTION OF THE DRAWINGS

In the accompanying drawings.

DESCRIPTION OF THE PREFERRED EMBODIMENTS

Figure 1:
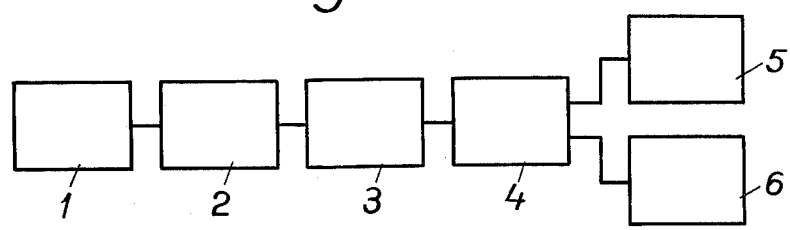
FIG. 1 shows a block diagram of the components comprising the system.

According to FIG. 1 the system comprises a measuring probe 1 which is designed to be easily and quickly mounted on the lance 2. The lance also carries a preamplifier 3. This is connected to a calculating unit 4 which may be arranged at a distance from the measuring point and which is designed to calculate the oxygen activity in the melt. A device 5 records and indicates this at the same time that the measurement takes place. The alarm device 6 gives a signal when the equipment is ready for measuring and when the measurement is complete. A group consisting of the units 4, 5 and 6 may serve several groups consisting of units 1, 2 and 3.

Figure 2:
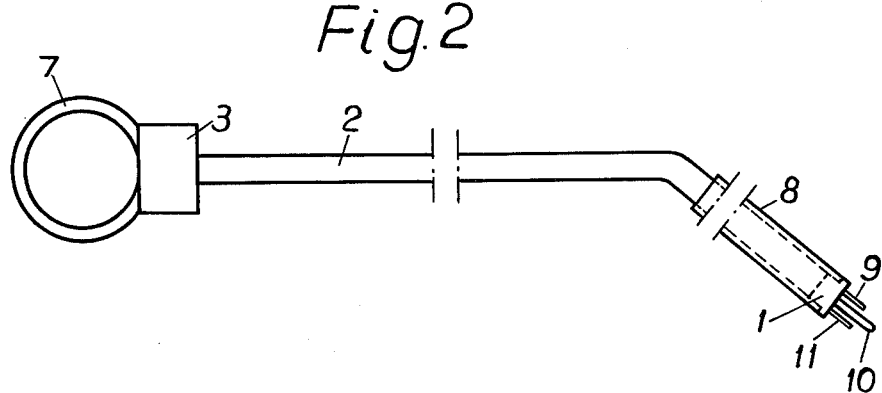
FIG. 2 shows the lance used for the measurement, with the measuring probe in place.

The lance 2 according to FIG. 2 is manufactured of steel tubing. At one end is a handle 7 by which to manipulate the lance during the measurement. The measuring probe is arranged at the other end of the lance and, in order to facilitate immersion of the probe into the melt, this end of the lance is bent at a suitable angle.

Figure 3:
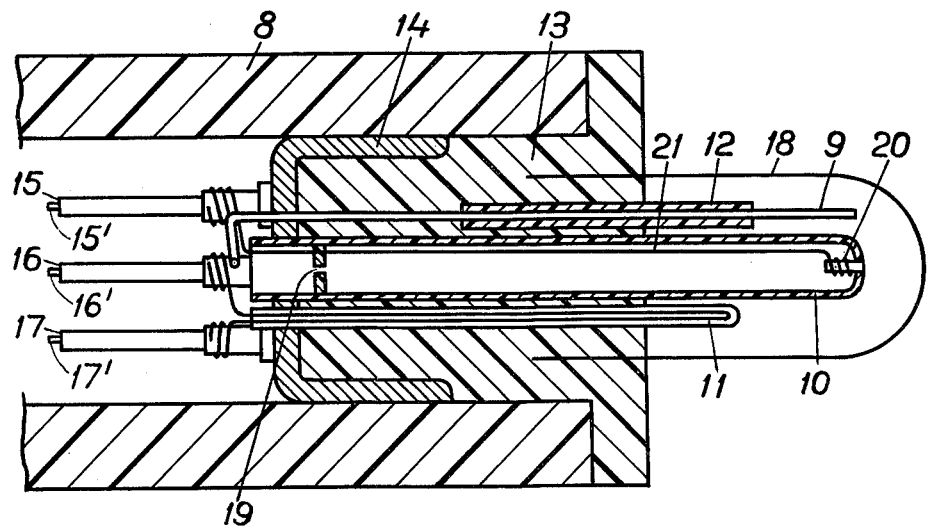
FIG. 3 shows a section through the measuring probe.

FIG. 3 shows a cross-section through the measuring probe 1. This is attached in one end of a paper sleeve 8 which surrounds the lower end of the lance and holds the probe in place on the lance. The measuring probe comprises an electrochemical cell and a thermoelement 11, both of which are attached in a socket 13 of ceramic material and inserted in and attached to the paper sleeve 8. The end of the socket situated inside the paper sleeve 8 has a holder 14 for a contact device comprising three contact sleeves 15, 16 and 17. The socket 13 has a protective lid 18 of readily meltable material which surrounds the electrochemical cell and the thermoelement in order to protect them during the first stage of the measurement when the probe penetrates through the layer of slag on top of the melt. The lid quickly melts so that this has gone when the probe reaches the melt.

The electrochemical cell consists of a silica tube 10 and a counter-electrode 9 which is arranged in the vicinity of the silica tube. The silica tube is attached in the socket 13. Its free end carries a body 20 of solid electrolyte which is attached in a hole in the silica tube. The part of the electrolyte projecting into the tube is connected by a conduit 21 to the contact 15 in the contact device of the probe. At its end facing away from the melt, the tube 10 is provided with a throttle 19 which keeps the air pressure in the tube substantially constant during the measurement and prevents foreign gases from penetrating into the tube effecting alterations in the oxygen reference. One conductor of the thermoelement 11 is connected to the contact 16 and the other conductor leads to the contact 17. Part of the counter electrode 9 projecting into the melt is surrounded by a casing 12 of a material having a higher melting point than the metal in the melt. This arrangement prevents the entire counter-electrode from melting away. The counter-electrode is electrically connected to the contact 16 in the contact device. All four conductors in the probe are therefore connected to the contacts 15, 16 and 17 in the contact device of the probe. The end of the lance which is pushed into the tube 8 has a contact device having three contact pins 15', 16', 17' fitting into the contact sockets in the contact device of the probe. Both the probe and the lance are suitably provided with guide means so that it is only possible to push the probe onto the lance completely in one position of the probe. It is thus ensured that the two contact devices will always be in the correct position in relation to each other.

The electrochemical cell forms a voltage source with extremely high inner impedance. This means that the signal from it must be taken out with the least possible current strength and the risk of disturbance to the signal is great. For this reason a high ohmic preamplifier is arranged as close to the signal source as possible. However, the high temperature prevailing in the melt must also be taken into consideration. An acceptable compromise is to arrange the preamplifier 3 near the manipulating handle of the lance. The connection of the four conductors of the probe to the contact devices as explained previously enables the information from both the electrochemical cell and the thermoelement to be transferred to the preamplifier through only three wires.

The signals amplified in the preamplifier are then transmitted to the calculating unit 4. This is placed far away from the measuring point in order to protect it from electrical and mechanical disturbances. In order still further to avoid the influence of external electrical disturbance and to enable measurements to be carried out in an electrically heated furnace, where the potential of the melt usually deviates from earth potential, the potential of the metal melt is selected as zero potential in the total measuring system during the measurement. This zero potential is withdrawn through the counter electrode 9.

The calculating unit 4 calculates the oxygen activity $a$ in ppm and the temperature in ° C with the help of the two EMF signals from the electrochemical cell and from the thermoelement. The unit is also designed to represent directly both the oxygen activity and the temperature of the melt, partly with a recording instrument and partly with an indicating instrument. The recording of the oxygen signal only starts when the temperature has reached a certain, adjustable level, for example 1400° C.

Figure 4A:
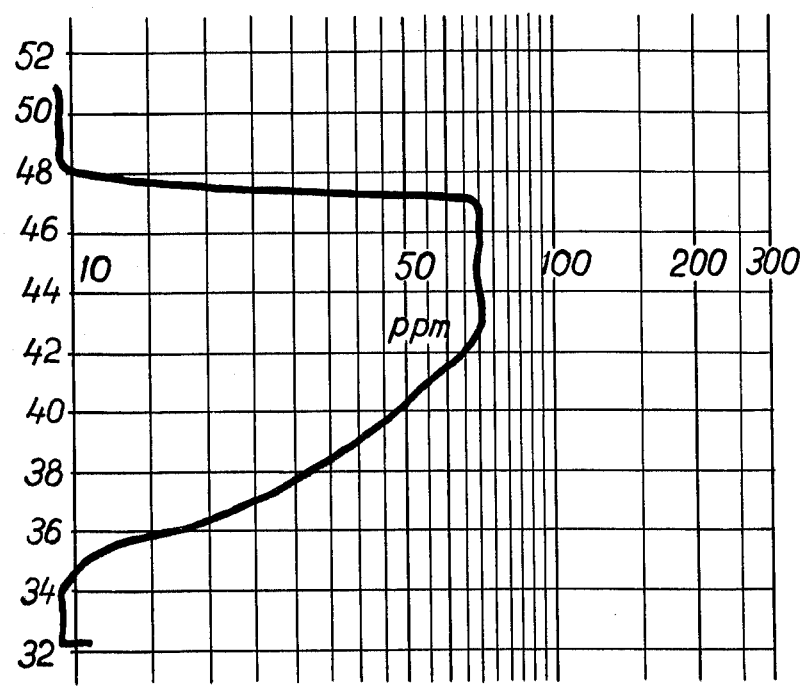
FIGS. 4a and 4b show by means of curves the result of a measurement using the system.
Figure 4B:
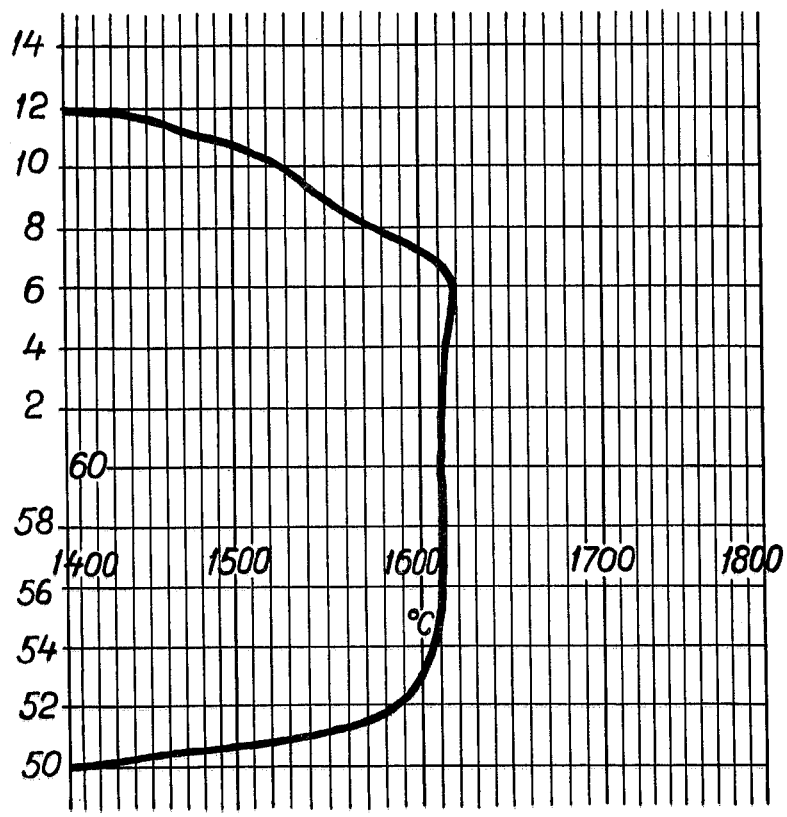

FIG. 4a shows the recording of the oxygen activity $a$ in a practical test in a steel melt. FIG. 4b shows the corresponding recording of the temperature of the melt.

Calculation of the oxygen activity $a$ is performed according to the formula:

$$\ln a = \frac{k_1}{k_2 \cdot V + k_3} [k_4 - k_5(k_6[k_2 \cdot V k_3] - k_7 + E) - k_8]$$

In a certain case with a melt of iron having a Pt-PtRh-(10%) thermoelement and a counter-electrode of iron, the constants $k_1 - k_8$ have the following values:

$k_1 = 10^4$
$k_2 = 0.8475 \cdot 10^5$
$k_3 = 0.457 \cdot 10^3$
$k_4 = 1.4043$
$k_5 = 2.3229$
$k_6 = 1.701 \cdot 10^{-5}$
$k_7 = 7.49 \cdot 10^{-3}$
$k_8 = 0.3824$ V is the EMF of the thermoelement E is the probe voltage which is determined by the expression $$E = -\frac{\Delta G°}{2F} - \frac{RT_k}{2F} \cdot \ln \frac{a}{\sqrt{P_{O_2}}} - E_T$$

$\Delta G°$ is the available energy in the reaction $\frac{1}{2} O_2 \rightarrow [O]_{Me}$ F is Faraday's constant 23066 cal/V and val.

R is the general gas constant 1.986 cal/mol degree.

$T_k$ is the temperature of the melt in ° K.

$a$ is the oxygen activity in %.

$P_{O_2}$ is the oxygen gas pressure kgf/cm² of the oxygen reference $E_T$ is a thermoelectric voltage deriving from different material in the probe.

The time taken for the measurement is about 10 seconds, 5 seconds of which is taken up to stabilize the measuring cell thermically.

After completion of the measurement the paper sleeve 8 is to a great extent carbonized. When the lance has been taken out of the furnace the expended probe is removed and a new probe fitted, after which a new measurement can be performed.

The system according to the invention is suitable for checking operation and for automatically regulating steel processes. The signal from the system is fed into a process control unit which, after additional process parameters have been fed in, enables rapid presentation of process data and quick control of the process.

We claim:

1. A system for instantaneously determining the oxygen activity in molten metals in an electrically heated furnace where the potential of the melt usually deviates from earth potential comprising a measuring probe (1) having an electro-chemical voltage-producing cell (9,10) disposed in the electrically heated furnace for contacting the melt, a thermoelement (11) and contact devices (15,16,17), a measuring lance (2) carrying the probe, a preamplifier (3) mounted on the lance, the lance having corresponding contact devices and connections for transferring values from the measuring probe to the preamplifier, a calculating unit (4) connected to the preamplifier to convert the EMF of the electro-chemical cell and the EMF of the thermoelement to magnitudes representing the oxygen activity and temperature, and an indicating instrument (5) for these magnitudes, and means to maintain the potential of the melt as the zero potential in the system.

2. A method for instantaneously determining the oxygen activity in molten metal or metal alloy in an electrically heated furnace where the potential of the melt usually deviates from earth potential, comprising inserting in the melt a measuring probe having an electro-chemical cell, thermoelement and contact devices, the probe being carried by a measuring lance and having corresponding contact devices and connections for transferring values from the measuring probe to a preamplifier fitted on the lance, simultaneously converting the EMF of the electro-chemical cell and the EMF of the thermoelement in a calculating unit connected to the preamplifier to signal magnitudes representing the oxygen activity and temperature and indicating these magnitudes, the potential of the melt being the reference potential for the cell, the preamplifier and the calculating unit.

3. A system as claimed in claim 1, in which the cell is a solid electrolyte electrochemical cell.

4. A method as claimed in claim 2, in which the cell is a solid electrolyte electro-chemical cell.

* * * * *